United States Patent [19]
Wong et al.

[11] Patent Number: 5,478,753
[45] Date of Patent: Dec. 26, 1995

[54] POSITIVE CALIBRATOR/CONTROL COMPOSITION FOR AN IGM SEROLOGY ASSAY AND AN IGM SEROLOGY ASSAY

[75] Inventors: T. Philip Wong, Westwood; Russell A. Hammond, Boylston, both of Mass.

[73] Assignee: PB Diagnostic Systems, Inc., Westwood, Mass.

[21] Appl. No.: 84,014

[22] Filed: Jun. 29, 1993

[51] Int. Cl.$^6$ .......................... G01N 33/96; G01N 33/532; G01N 33/563

[52] U.S. Cl. .................. 436/513; 436/8; 436/15; 436/16; 435/967; 435/972; 530/391.1; 530/863

[58] Field of Search ................. 435/5, 967, 972; 436/513, 524, 8, 16, 15; 530/391.1, 863

[56] References Cited

U.S. PATENT DOCUMENTS

| | | | |
|---|---|---|---|
| 4,292,403 | 9/1981 | Duermeyer | 435/5 |
| 4,433,059 | 2/1984 | Chang et al. | 436/512 |
| 5,008,183 | 4/1991 | Osther | 435/5 |

*Primary Examiner*—Christine M. Nucker
*Assistant Examiner*—Julie Krsek-Staples
*Attorney, Agent, or Firm*—Tatsuya Ikeda

[57] ABSTRACT

There is described a positive calibrator/control composition for use in assays for the detection of antibodies to infectious disease agents. The composition includes a composite antibody of a nonspecific IgM immunoglobulin moiety covalently linked to a specific, non-IgM antibody moiety. Also described is an assay method which utilizes the positive calibrator or control composition.

18 Claims, 1 Drawing Sheet

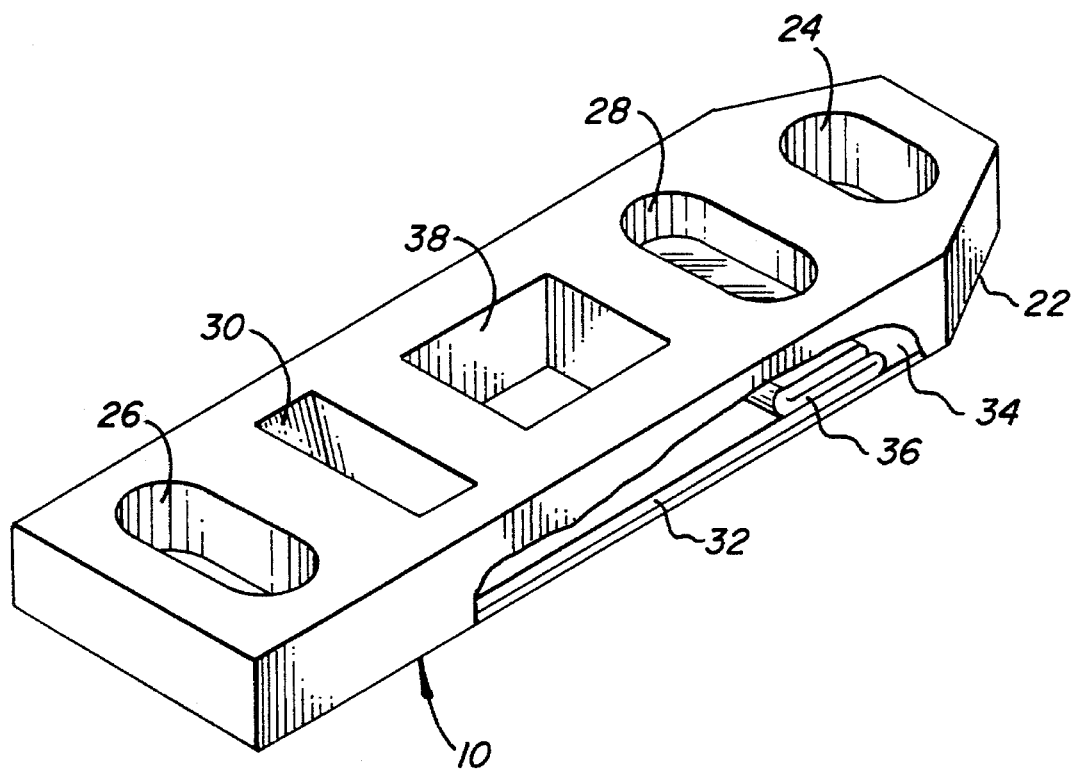
Figure

POSITIVE CALIBRATOR/CONTROL COMPOSITION FOR AN IGM SEROLOGY ASSAY AND AN IGM SEROLOGY ASSAY

BACKGROUND OF THE INVENTION

The invention relates to a positive calibrator/control composition for IgM serology assays and to an IgM serology assay using the positive calibrator/control composition.

Assays for infectious diseases require both negative and positive calibrator and/or control compositions. The negative calibrators typically consist of human sera which are known not to include any of the antibodies of interest. The positive calibrator compositions typically are prepared by spiking the negative calibrators with known amounts of the antibodies of interest which are obtained from human patients. The positive control compositions typically are prepared by spiking the negative calibrators with amounts of the antibodies which are equal to or different from those which are used in the calibrator compositions.

It is well known that the first immune response to an infectious disease agent in an individual is the production of IgM antibodies. However, the IgM immune response occurs only for a very short period of time, e.g., for a few weeks to a few months. The IgG immune response follows and goes on for a relatively long period of time, e.g., a number of years.

Since the first immune response is the production of IgM antibodies, and because IgM antibodies are short-lived, assays for these antibodies are important since such assays can provide an early indication of a recent infection in a patient. However, because of the short duration of the IgM response and the fact that the infectious disease in a patient may not be discovered until the IgM response has ended, it is difficult to obtain a sufficient supply of IgM antibodies from individuals to use in positive calibrator/control compositions for assays for the infectious disease. Further, the procedure for doing so is labor intensive, very lengthy and very costly.

It would be advantageous to have an unlimited supply of antibodies of consistent quality which can be used in the positive calibrator/control compositions for IgM serology assays. Accordingly, it is an object of this invention to provide a positive calibrator/control composition for use in IgM serology assays. It is also an object of the invention to provide an IgM serology assay which utilizes the positive calibrator/control compositions according to the invention.

SUMMARY OF THE INVENTION

These and other objects and advantages are accomplished in accordance with the invention by providing a positive calibrator/control composition for use in an assay to detect antibodies to infectious diseases, which includes a nonspecific IgM immunoglobulin covalently linked to a non-IgM antibody which is specific to the infectious disease agent of interest. As will be described in detail, the binding properties of both the nonspecific IgM immunoglobulin and the specific antibody segments of the composite antibody of the invention are exploited in the diagnostic assay. The nonspecific IgM immunoglobulins may be from humans or from animals which produce immunoglobulins which are highly homologous to those produced in humans and which exhibit substantially the same binding behavior as nonspecific human immunoglobulins. Nonspecific IgM immunoglobulins are present in individuals at all times and therefore can be obtained without difficulty. The antibodies which are specific to the infectious disease agent of interest may be of any class, i.e., IgG, IgA, IgD or IgE. The specific IgG antibodies are preferred since they are abundant and are present in individuals for a long period of time, due to the long duration of the IgG response to the infectious disease agent.

The calibrator compositions are typically used to determine a reference signal cutoff value for the particular analytical apparatus used to carry out the assay. The control compositions are typically used to check whether assay elements from a particular production lot are useful for their intended purpose and to assure that the analytical apparatus is functioning properly. The control compositions may contain an amount of the composite antibody according to the invention which is equal to or different from the amount present in the calibrator compositions.

In the assay method of the invention, there is immobilized to a solid carrier a capture material which is selected to bind specifically to the composite antibody present in the positive calibrator/control composition. Generally, the positive calibrator/control composition, or a fluid sample which is suspected of containing the IgM antibodies of interest, and a labeled conjugate are brought into contact with the solid carrier material. The conjugate comprises a label moiety, which may be directly or indirectly detectable, linked to a detector material which is selected to bind to the composite antibody and to the antibodies of the infectious disease agent of interest which may be present in a sample fluid. Subsequently, after a period of time to allow the requisite binding interactions to take place, unbound labeled conjugate is separated from bound labeled conjugate and a signal generated as a function of the label of the free or bound conjugate. The signal can be utilized to calibrate the analytical instrument in the case of the positive calibrator/control composition or to determine the presence of and/or the amount of antibodies of interest in the case of a test sample.

The positive calibrator/control composition and assay method of the invention may be used for any IgM serology assay, that is, any assay for antibodies to an infectious disease. Typical infectious diseases for which IgM screening may be carried out include rubella, cytomegalovirus, toxoplasma, lyme disease, herpes I and II, Epstein-Barr virus, HTLV, HIV, syphilis, hepatitis and varicella zoster virus (vzv).

The assay method of the invention is sensitive and specific, and in a preferred embodiment can be carried out in a single test module format which allows for total test containment. Further, there is provided, according to the preferred embodiment wherein the solid carrier has a relatively large surface area, such as in the case of a fibrous solid carrier, rapid capture through a relatively large amount of binding material and a less vigorous and less technique-dependent wash due to a relatively low concentration of the labeled detector material. In addition, there is provided for use in the assays a virtually unlimited supply of composite antibodies for dse in the positive calibrator and control compositions.

BRIEF DESCRIPTION OF THE DRAWING

For a better understanding of the invention, as well as other objects and further features thereof, reference is made to the following detailed description of various preferred embodiments thereof taken in conjunction with the accompanying drawing, wherein FIG. 1 is a simplified isometric view of a single test module which can be utilized for the assay method.

DESCRIPTION OF THE PREFERRED EMBODIMENTS

As mentioned previously, the nonspecific IgM immunoglobulins may be from humans or from animals which are closely phylogenetically related to humans. Such animals, e.g., primates and pigs, produce immunoglobulins which are highly homologous to those produced in humans and which exhibit substantially the same binding behavior. The nonspecific IgM immunoglobulins, which are incorporated into the composite antibodies provided according to the invention, can be obtained according to methods which are well known to those skilled in the art. Typically, this is carried out by a technique known as differential precipitation wherein undesired components of serum are precipitated out by the addition of saturated ammonium sulfate solution and discarded. The supernatant ammonium sulfate solution is then treated to precipitate the desired nonspecific IgM immunoglobulins which are then dissolved for use.

The nonspecific IgM immunoglobulins used in the composite antibodies may be the whole immunoglobulin or only the Fc region (μchain) which binds to the capture material on the solid carrier. Further, it is not necessary to highly purify the IgM immunoglobulins used to form the composite. It is preferred to purify the IgM solution to a concentration of about 80% or more.

The specific, non-IgM antibodies incorporated in the composite antibodies of the invention may be monoclonal or polyclonal and may be obtained from humans or from animals. The latter must provide antibodies which are specific to the infectious disease agent of interest and which will bind to the detector material present in the conjugate. Such specific antibodies may be obtained from any animal which has been exposed to, or immunized with, the etiologic agent of interest or a fragment of the etiologic agent. Preferred animals for this purpose are rabbits, goats and mice. For polyclonal specific antibodies, it is preferred to use IgG antibodies since they are abundant and readily available. Polyclonal IgG antibodies may be partially purified from serum components by differential precipitation with ammonium sulfate or protein G chromatography columns. Specific polyclonal IgG antibodies may be highly purified with affinity chromatography columns. Monoclonal antibodies of all classes, i.e., IgG, IgA, IgD and IgE, are readily available. The whole specific, non-IgM antibodies can be utilized or the Fab or the F(ab')$_2$ segments thereof.

The specific, non-IgM antibodies can be raised in animals according to methods which are well known to those skilled in the art and therefore extensive discussion of such techniques is not required here. Typically, an immunization solution or suspension is prepared by forming a solution or suspension containing a substance capable of stimulating antibody production in a host animal, e.g., microbial particles such as whole or disrupted viral, bacterial or parasitic particles, recombinant antigens, or synthetic peptides, the sequence of which has been identified from the infectious disease etiologic agent, in a base fluid. The solution or mixture is buffered to the desired pH with a suitable buffer such as phosphate buffered saline (PBS), pH 7.3. The first injection is made with an aliquot of the solution or mixture to which an adjuvant which stimulates the immune response of the animal, such as complete Freund's adjuvant, has been added. In subsequent booster immunizations it is preferred to use aliquots of the immunization solution or mixture to which an adjuvant such as incomplete Freund's adjuvant has been added. Typically, the immunization regimen includes at least three booster immunizations at weekly intervals beginning a week after the initial immunization. The immunizations may be administered by any suitable mode including subcutaneously and intramuscularly.

Serum is collected from the host animal following the immunization regimen and tested according to a known assay method for the infectious disease of interest. A sufficiently high antibody titer is indicated by a positive result on the assay. When the antiserum meets the required specifications, the antiserum is typically collected from the animal at intervals. Of course, those skilled in the art will recognize that the requisite antibody titer will vary according to the assay method for which the positive calibrator or control solution is desired.

The antisera obtained may or may not be treated before use such as to inactivate any live infectious agent which may be present. These antisera are typically diluted many fold, for example, a thousand fold, in a base fluid such as processed human off-clot serum. The solution may include additives such as an anti-microbial agent as a preservative. The concentration of any particular positive calibrator or control composition will be dependent upon the cut off signal value determined for the assay method.

The human nonspecific IgM immunoglobulins and the specific, non-IgM antibodies can be covalently bonded to each other by any of many suitable techniques and these will be apparent to those skilled in the art, particularly in view of the examples provided herein. Generally speaking, the covalent binding procedure should be carried out to ensure that the antigen-binding sites of the specific non-IgM antibodies and/or those of the nonspecific IgM immunoglobulins are available for binding to the labeled conjugate or the capture material on the solid carrier. Thus, the covalent binding preferably is not through the Fab segment of the non-IgM antibodies.

The composite antibodies may be synthesized by reacting the specific, non-IgM antibodies and the nonspecific IgM immunoglobulins at various molar ratios, e.g., from about 1:1 to about 5:1 non-IgM/IgM. The preferred molar ratio in any specific instance is dependent upon various factors including the synthetic conditions and reagents and the assay format in which the positive calibrator/control composition is intended to be used. The size of, and the non-IgM/IgM ratio in, the resulting composite antibodies may be heterogeneous due to molecular cross-linking and may be dependent upon the cross-linking conditions and the reagents used. It is preferred to utilize a 2:1 molar ratio of non-IgM/IgM in the reaction procedure.

One method for synthesizing the composite antibodies according to the invention involves initially reacting the nonspecific IgM immunoglobulins with a reagent which will react with primary amines to introduce sulfhydryl groups on proteins. A suitable reagent for this purpose is 2-iminothiolane (2-IT; Traut's reagent). The specific, non-IgM antibodies are reacted with a heterobifunctional reagent such as N-γ-maleimidobutyryloxysuccinimide (GMBS) to introduce maleimide groups on the antibodies. These maleimide groups are available for reaction with proteins containing free sulfhydryl groups to yield covalently coupled protein conjugates.

The conjugation reaction can be carried out by reacting the GMBS-activated non-IgM antibodies with the 2-IT-activated nonspecific IgM immunoglobulins at a 2:1 molar ratio (non-IgM:IgM) for about 18 to 24 hours at a temperature of about 2° to 8° C. The reaction is quenched with 2-mercaptoethylamine and N-ethylmaleimide. After quenching, the composite antibodies are dialyzed into a buffered saline solution, pH 7.6, and the dialyzed composite antibody solution is diluted with an equal volume of a nonreactive serum which is not reactive to the infectious disease agent of interest. The resulting composite antibody solution is used as the reactive stock solution for which a titer is assigned.

The titer of the reactive stock solution is determined using the analytical method and apparatus used to assay the unknown fluid samples. Generally, several dilutions of the reactive stock solution are prepared in nonreactive human serum and each dilution assayed together with the reactive and nonreactive reference standards. A dilution factor is assigned to the reactive stock solution based on the data collected to prepare the reactive calibrator or control.

According to a preferred embodiment of the invention, there is provided a positive calibrator/control composition which can be used for a plurality of IgM serology assays. For example, a calibrator/control composition can be provided for use with toxoplasma, rubella, cytomegalovirus and herpes antibody assays by incorporating in the composition composite antibodies for each specific antibody of interest. Advantageously, one calibrator/control composition can be provided for use with a plurality of assays instead of requiring a separate calibrator/control composition for each assay.

The assay method of the invention also involves the use of a labeled detector material. The detector material in the labeled conjugate may be any which will bind to the antibodies of interest and to the composite antibody present in the positive calibrator/control composition. It will be understood, of course, that the detector material should not exhibit any substantial binding to any specific IgM antibodies which may be present in a test fluid other than the specific IgM antibodies for which the assay is conducted. The detector material may be of any type including recombinant or purified cultured antigens, e.g., extracts from the entire infectious disease agent which may be a virus, bacterium, fungus, protozoa, etc., analogues thereof, synthetically prepared peptide sequences or recombinant proteins. Typical suitable binding materials which can be incorporated into the labeled conjugate include, for example, monoclonal and polyclonal anti-human IgM antibodies, lectins such as mannan binding protein and chick pea lectin and the like. Monoclonal antibodies and synthetically prepared peptide sequences are preferred because of their binding specificity. For HIV assays it is preferred to utilize labeled HIV I and II peptide sequences because of their lack of cross-reactivity and safety in handling.

Any of the labels known for use in immunometric assays may be utilized including, for example, fluorescent moieties, enzymes, chemiluminescent moieties and radioactive materials. Any change in fluorescence, chemiluminescence, radioactivity or other change in visible or near visible radiation can be exploited. Thus, the label may be directly or indirectly detectable. Where the label is an enzyme it can be one which interacts with a substrate to cause a change in absorption where the substrate is a chromogen, in fluorescence if the substrate is a fluorophore, in chemiluminescence where the substrate is a chemiluminescent precursor or in phosphorescence where the substrate is a phosphor. It is preferred to utilize enzyme labels because of the amplification of the signal which is obtained.

The assay method according to the invention may exploit any solid phase assay technique so long as the solid phase is capable of capturing the composite antibodies of the positive calibrator/control composition and the antibodies of interest in a test sample. The capture material immobilized to the solid carrier may be selected from the materials described with respect to the detector material of the labeled conjugate. Any suitable material can be used as the capture agent, including monoclonal antibodies directed against human IgM antibodies.

The solid carrier may be of any suitable type, including microtiter plates, beads such as of polymeric material, magnetic material or glass, porous materials such as membranes or fibrous materials such as glass and the like. Further, any suitable assay technique may be practiced, including the "forward" assay technique wherein the sample fluid is applied to the solid carrier, followed after the period of incubation by application of a labeled conjugate solution and the "reverse" assay technique wherein the sample fluid is first combined with a labeled conjugate solution to form a complex and the resulting complex is applied to the solid carrier.

As described previously, the assay method of the invention can exploit the binding characteristics of both the nonspecific IgM immunoglobulin and the specific, non-IgM antibody segments of the composite antibodies in the positive calibrator/control composition. In one embodiment the capture material immobilized on the solid carrier, for example, a monoclonal antibody, is selected so as to bind to the nonspecific IgM immunoglobulin segment of the composite antibody (and also to the infectious disease antibody of interest). In this embodiment the detector material (e.g., an extract or fragment of an etiologic agent) incorporated in the labeled conjugate is selected to bind to the specific, non-IgM antibody segment. This embodiment is particularly preferred when the solid carrier material has a relatively large surface area such as that present in a fibrous filter material.

In another embodiment the capture material immobilized on the solid carrier can be selected to bind to the specific, non-IgM antibody segment of the composite antibody and to the infectious disease antibodies of intereset. In this embodiment the detector material in the labeled conjugate, e.g., an anti-human IgM antibody, is selected to bind to the nonspecific IgM immunoglobulin segment of the composite antibody. This embodiment is particularly preferred for use with microtiter plate assays.

The invention will now be described further in detail with respect to a particularly preferred assay technique according to the invention wherein a porous material is used as the solid carrier. In this preferred embodiment it is preferred that the porous member have a relatively large surface area to allow for the capture of the IgM antibodies present in any sample fluid. The porous member may be a porous membrane, a fibrous mesh pad or the like and may be of any suitable material such as glass, polymeric materials, paper, etc.

As noted previously, there is immobilized to the porous member a binding, or capture, material capable of binding to IgM immunoglobulins and also to the composite antibodies in the positive calibrator/control compositions. Any of the suitable binding materials mentioned above may be used. The amount of binding material necessary for any particular assay varies with the assay and can be optimized by conventional experimental scoping techniques. It is preferred to calculate the amount of binding material necessary to bind all, or substantially all, of the IgM antibodies in the patient sample and apply an excess of that amount to the porous member.

The binding material may be applied to the porous member and immobilized thereto by any of various known techniques including physical entrapment and chemical bonding. For example, a solution of the binding material can be applied to the porous member and the member subsequently dried to provide a porous member having the binding material distributed throughout and held therein by the structure of the member. In another embodiment, particularly where the porous member comprises a fibrous mesh material, the binding material can be chemically bound to or adsorbed on polymeric particles and the fibrous mesh pad impregnated with the particulate matter. In this manner the binding material is immobilized to the porous member and remains there throughout the assay method. A preferred technique is to apply a solution of the binding material to the porous member and subsequently heat the member to fix the binding material thereto.

The method of the invention may be practiced in various embodiments. In one embodiment the test sample may be applied initially to the porous member followed by an incubation step to allow the specific IgM antibodies in the sample fluid to interact and bind to the binding material on the porous member. A solution of the conjugate is then applied to the porous member followed by an incubation step. In another embodiment, a volume of fluid sample, e.g. about 30 µl, is added to a solution of the labeled conjugate in a buffer, and the mixture incubated to allow the interactions between the labeled conjugate and antibody of interest to take place. An aliquot of this reaction mixture is then deposited on the porous member followed by another incubation step to allow the interactions between the binding material and the antibodies in the fluid sample to occur.

After the interactants have been brought together in the reaction zone and allowed to interact under the appropriate conditions for the requisite period of time, any free labeled conjugate is removed from the reaction zone such as by a wash step wherein a wash solution is applied to the porous member.

Subsequently, any bound labeled conjugate is detected by appropriate means. As described previously, the label maybe directly or indirectly detectable. In the case of an enzyme label the substrate solution which is applied to the porous member to render the label detectable may also be utilized as the wash solution to remove from the porous member any free labeled conjugate.

In a particularly preferred embodiment of the invention the method is practiced with a single test capillary assay module which is suitable for use in automated analytical test instruments. Referring now to the Figure there is illustrated a self-contained assay module, or element, 10 which carries all of the test reagents, except for the sample fluid, or calibrator/control composition necessary for a particular assay. This preferred assay element includes a plurality of chambers in a housing 22 wherein a first chamber serves as a front reservoir 24 for the storage of the labeled conjugate solution. The solution is covered with a frangible or puncturable foil layer (not shown). A second of the chambers serves as a back reservoir 26 for the storage of a substrate solution which is also covered with a similar foil layer (not shown). An optional third chamber serves as a mixing bowl 28 for the mixing of reagents and a fourth chamber forms part of a dispenser 30 which is utilized to dispense the substrate solution to one end of the porous member 32. There is also shown a chamber 34 within the housing 22 wherein there is arranged an absorbing material for absorbing fluid removed from the porous member such as by a wash fluid as it propagates through the porous member 32.

In this preferred embodiment the porous member 32 is a thin porous member possessing an intercommunicating network of openings throughout such that a fluid deposited on the member will propagate throughout the member because of capillary action. The thin porous member 32 may be any suitable element such as a porous membrane, a fibrous mesh pad or the like and may be of any suitable material such as glass, polymeric materials, paper, etc. In a particularly preferred embodiment porous member 32 comprises a non-woven glass fiber mesh having very thin fibers such as on the order of about 1 micrometer.

The porous member 32 is mounted within a guide (not shown) formed within the housing 22 and having top and bottom surfaces which are spaced apart a distance sufficient to support the member 32. By way of example, the spacing between the top and bottom surfaces of the guide may be in the range of from about 0.30 mm to about 0.60 mm; the preferred spacing is about 0.40 min.

The porous member 32 extends from the dispenser 30 to the chamber 34 which holds the absorbing material. The dispenser chamber 30 is configured as a well for holding a fluid, the dispenser 30 including a port at the bottom of the well and means for allowing communication of fluid from the bottom of the well into the porous member 32. Liquid absorbing material 36, which may be any suitable material, is located within chamber 34 and forms a part of the chamber 34 for taking up fluid expelled from the porous member 32 and the guide area, or reaction zone. Absorbing material 36 is located contiguous porous member 32 and in a preferred embodiment (as illustrated) is formed conveniently as an extension of the porous material folded back and forth on itself.

The housing 22 also preferably includes a chamber 38 which is positioned immediately above the top horizontal surface of porous member 32 and has a port at the bottom periphery thereof to allow fluid to be delivered to the porous member 32. The housing 22 may include a transparent window area (not shown) positioned immediately below the bottom horizontal surface of porous member 32 to provide access for the illumination used to measure any detectable change effected in the porous member as a result of the assay method or preferably an opening in the housing to permit readout illumination to be directed onto the porous member without having to pass through the material of which the housing is comprised.

The sample fluid tested according to the assay method of the invention may be any including whole blood, plasma or serum. According to a preferred embodiment a small amount, e.g., about 20 µl of serum taken from a patient sample is added to the porous member 32 through chamber 38 via a pipette and the assay element is allowed to incubate for the necessary period of time. It will be understood that the amount of patient sample required can vary from assay to assay. Subsequently, enzyme-labeled conjugate solution in chamber 24 (e.g., 20 µl) is aspirated into a clean pipette tip which has perforated the foil layer over chamber 24 and then deposited on the surface of porous member 32 through chamber 38. The assay module is again allowed to incubate for a suitable period to allow the interactions to take place. Subsequently the foil layer covering chamber 26 to form a seal over the substrate solution in the chamber is perforated by a pipette carrying a clean tip and a desired volume of the substrate solution, typically about 90 µl, is aspirated into the pipette tip. The substrate solution is then deposited into chamber 30 from where it is allowed to come into contact with one end of porous member 32 and then drawn throughout the member by capillary action. The assay module is then allowed to incubate to permit the reaction between the substrate material and any bound enzyme label to take place. It is apparent that the substrate solution is also utilized as a wash fluid in this embodiment. As the substrate solution propagates through porous member 32 it forces any free enzyme-labeled conjugate together with the fluid out of the porous member and into absorber chamber 34 where they are taken up by absorber material 36. The signal provided by the species liberated by the reaction between the substrate material and the enzyme, for example, a fluorescent species, is then read by means of a suitable readout means, e.g., a fluorometer. Both qualitative and quantitative results can be obtained with this method. The method of the invention as carried out with the preferred assay module illustrated can be practiced with an automated assay instrument thus providing a totally self-contained test which requires a minimum of operator involvement and which eliminates operator variability.

The assay method involves the use of negative and positive calibrators as pointed out previously. Generally, there is determined a reference signal cutoff value for the particular apparatus employed to carry out the assay. The reference cutoff value may be determined in accordance with various techniques which are known in the art. For example, a cutoff value can be obtained by preparing a dose response curve. However it is determined the reference cutoff value is then validated by testing large numbers of known positive and negative clinical samples.

The invention will now be described further in detail with respect to specific preferred embodiments by way of examples, it being understood that these are intended to be illustrative only and the invention is not limited to the materials, conditions, procedures, etc. recited therein.

EXAMPLE 1

Purification of IgM from Human Serum

To 500 ml of anti-toxoplasma negative serum there was added a saturated ammonium sulfate solution (pH 7.0) to 30%, by volume, with stirring over a 20 minute period. After stirring for an additional 30 minutes the solution was centrifuged for 20 minutes at 3000×g. The ammonium sulfate supernatant liquid was decanted into a clean container and brought to 50% with saturated ammonium sulfate solution. The solution was stirred for an additional 30 minutes and then centrifuged for 20 minutes at 3000×g.

The supernatant liquid was discarded and the IgM pellet was suspended in 50 ml of a 20 mM sodium phosphate solution (pH 7.0). The conductivity of the IgM solution was adjusted to approximately the same conductivity as a 0.16M ammonium sulfate solution by diluting the IgM solution with distilled water. The IgM immunoglobulins were precipitated from solution by adding a 24% solution of polyethylene glycol (average molecular weight 8000) to a final concentration of 6%. Stirring was then continued for 30 minutes followed by centrifugation at 3000×g for 30 minutes. The supernatant liquid was discarded and the IgM pellet was dissolved in 250 ml of 50 mM Tris buffer (pH 7.6), 150 mM NaCl followed by extensive dialysis against the same buffer. After the dialysis step the IgM solution was filtered through a 0.8 μm filter, then a 0.45 μm filter and finally a 0.2 μm filter. About 0.1% of a preservative, Kathon, was added and the solution stored at a temperature of about 2° to 8° C.

EXAMPLE II

Purification of Rabbit IgG

About 5 to 15 mL of a rabbit anti-toxoplasma serum were applied to a recombinant protein G-sepharose column equilibrated in phosphate buffered saline (PBS)—20 mM sodium phosphate, 150 mM NaCl, pH 7.2. After the sample was loaded on the column it was washed with 50 ml of PBS. The IgG was eluted from the column with 0.1M glycine, pH 2.5. Ten 5 mL fractions were collected into tubes containing 0.5 mL of 2M Tris buffer, pH 8.0. The absorbance of each fraction at 280 nm was determined and the fractions with absorbance above 0.7 were pooled and dialyzed against 50 mM Tris, 150 mM NaCl, pH 7.6. After dialysis the rabbit IgG was filtered through a 0.2 μm filter and a preservative, 0.1% Kathon, was added. The purified rabbit IgG was stored at a temperature of about 2° to 8° C.

EXAMPLE III

Conjugation of Rabbit IgG to Human IgM

Approximately 60 mg of human IgM and 20 mg of rabbit anti-toxoplasma IgG were each concentrated to about 8 to 10 mg/ml using an Amicon Centripep 30. Both antibody solutions were dialyzed against a PE buffer (0.1M sodium phosphate, 1 mM EDTA, pH 7.0).

The rabbit IgG antibodies were activated with GMBS by adding a 20 mg/ml solution of GMBS in dimethylformamide to the IgG solution at a 20:1 molar ratio (GMBS:IgG) and the solution incubated for 60 minutes at 30° C. The activated IgG was purified from residual GMBS by putting the reaction mixture through a PD 10 column (Pharmacia) into PE buffer solution. Fractions of 1 ml were collected and those having an absorbance at 280 nm greater than 0.7 in the first peak were pooled.

The human IgM was activated with 2-iminothiolane by adding 100 mM of 2-IT in distilled water to the IgM solution to a final concentration of 5 mM 2-IT by adding a 1/20th volume of 100 mM 2-IT. The reaction mixture was incubated for 20 minutes at room temperature followed by addition of 100 μl of 1M glycine to the reaction mixture and incubation for 5 minutes. The activated IgM was purified from residual 2-IT by putting the reaction mixture through a Sephadex G-25 column into PE buffer solution and 1 ml fractions were collected. The fractions with an absorbance (at 280 nm) greater than 0.5 in the first absorbance peak were pooled.

The GMBS-activated rabbit IgG antibody solution was added to the 2-IT activated human IgM solution at a 2:1 molar ratio (IgG:IgM) and the reaction mixture incubated for about 18 to 24 hours at a temperature of about 2° to 8° C. The conjugation reaction mixture was quenched by adding 1/100th volume of 100 mM 2-mercaptoethylamine in PE buffer solution followed by incubation for 30 minutes at room temperature and the addition of 1/100th volume of a 25 mg/ml solution of N-ethylmaleimide in dimethylformamide. The reaction mixture was then incubated for 30 minutes at room temperature and the conjugate dialyzed in 50 mM Tris, 150 mM NaCl, pH 7.6.

To the conjugate solution there was added an equal volume of a negative anti-toxoplasma serum. The solution was then filtered through a 0.2 μm filter and Kathon was added to a concentration of about 1%.

The composite antibodies were used as positive calibrators and controls for the assays carried out in the following examples.

EXAMPLE IV

Assays for composite nonspecific IgM/specific non-IgM antibodies in the reactive calibrator or specific IgM in patient samples of serum or plasma to *Toxoplasma gondii* were carried out according to the method of the invention in accordance with the following procedure. A solution of monoclonal antibody to human IgM at a concentration of 1.25 mg/ml in 50 mM TRIS buffer, pH 7.5, 0.1% Triton X-100 and 0.1% Kathon, was prepared and 25 µl were applied to an approximately 1 cm. sq. porous glass fibrous mesh pad, Ahlstrom #161, at chamber 38 in an assay module of the type illustrated in the Figure. The amount of binding material applied to the mesh was calculated to be theoretically in excess of that required to bind all of the IgM in a typical patient sample. The assay module was dried at above room temperature to fix the binding material to the fibrous pad.

A total of 20 µl of calibrator or sample was added to the fibrous pad at the area coated with binding material followed by a 6 minute incubation at 37° C. to allow the binding material to capture IgM. To the area of the fibrous pad coated with the binding material was added 20 µl of a Toxoplasma antigen extract which was previously covalently conjugated to alkaline phosphatase and diluted to the desired concentration in a buffer consisting of 50 mM TRIS, pH 7.6, 150 mM NaCl, 1 mM $MgCl_2$, 0.1 mM $ZnCl_2$, 8 mM $CaCl_2$, 20 U/ml heparin, 0.1% Triton-X-100, 1% gelatin, 1% BSA and 0.1% Kathon. The reactants were incubated at 37° C. for 6 minutes to allow capture of the enzyme labeled antigen by specific antibodies. Subsequently, 90 µl of a substrate/wash solution consisting of 1 mM methyl umbelliferyl phosphate, 1 mM $MgCl_2$, 0.5M NaCl, 10 mM levamisole. HCl, 5 mM phenylalanylglycylglycine, 0.5M TRIS, pH 9.5, and 0.1% Triton X-100 was added to the wash port, chamber 30, of the module. The substrate/wash solution was allowed to enter the fibrous pad and propagate through it by capillary action thereby washing the sample area for a total of 6 minutes at 37°.

A reading was taken of the reaction zone after the six minute time period and a second reading was taken 300 seconds later using a front surface fluorometer by directing 360 nm radiation through an opening in the assay module beneath the reaction zone and collecting the reflected 450 nm radiation. The increase in fluorescence, a function of the amount of bound enzyme-labeled conjugate, was calculated. The result obtained was compared to the results obtained with a defined negative calibrator and the positive calibrators described in Example III and was determined thereby to be positive or negative on the basis of a determined cutoff value.

A total of 382 patient samples were tested for Toxoplasma-M on an OPUS® Immunoassay analyzer (PB Diagnostic systems, Inc). A positive calibrator composition which included human anti-Toxo-M antibodies was used together with a negative calibrator to establish the cutoff value. For comparison purposes the patient samples were also tested with an indirect fluorescent antibody (IFA) test kit from Gull Laboratories. The results are shown in Table I.

TABLE I

|  |  | GULL TOXO-M IFA | |
|---|---|---|---|
|  |  | NEGATIVE | POSITIVE |
| OPUS TOXO-M | NEGATIVE | 277 | 3 |
|  | INDETERMINATE | 12 | 6 |
|  | POSITIVE | 16 | 68 |

It is seen that of the 71 samples detected as positive by the Gull test kit (the 6 samples found to be indeterminate not being included in accordance with standard industry practice) the OPUS assay module detected 68 as positive. Thus, the OPUS assay module sensitivity (compared to the Gull IFA) was 95.8% (68/71).

Further, it is seen that of 293 samples found to be negative by the Gull test kit (discarding the 12 indeterminate results), the OPUS assay module detected 277 as negative. Thus, the OPUS assay module specificity (compared to the Gull IFA) was 94.5% (277/293).

Both the sensitivity and specificity of the OPUS assay module are within accepted industry standards.

EXAMPLE V

A cutoff value was determined on an OPUS Immunoassay Analyzer using a negative calibrator composition and a positive Toxo-M calibrator composition according to the invention. The signal values obtained for the 382 patient samples assayed with the OPUS Analyzer and with the Gull IFA in Example IV were compared with the cutoff value obtained with the positive calibrator having the composite antibodies according to the invention. The results are shown in Table II.

TABLE II

|  |  | GULL TOXO-M IFA | |
|---|---|---|---|
|  |  | NEGATIVE | POSITIVE |
| OPUS TOXO-M | NEGATIVE | 269 | 2 |
|  | INDETERMINATE | 16 | 3 |
|  | POSITIVE | 20 | 72 |

It is seen that of 74 samples found to be positive by the Gull test kit the OPUS assay module detected 72 as positive. Thus, the OPUS assay module sensitivity (with the positive calibrator composition of the invention) was 97.2% (72/74) compared to the Gull IFA.

It is also seen that of 289 samples found to be negative by the Gull IFA, the OPUS assay module detected 269 as negative, giving it a specificity of 93.1% (269/289) compared to the Gull IFA.

Both the sensitivity and specificity of the OPUS assay module, in combination with the positive calibrator composition of the invention, are within accepted industry standards.

Although the invention has been described with respect to various specific preferred embodiments it is not intended to be limited thereto but rather those skilled in the art will recognize that variations and modifications may be made therein which are within the spirit of the invention and the scope of the appended claims.

What is claimed is:

1. A positive calibrator or control composition for an IgM serology assay comprising a solution of a composite antibody of a nonspecific IgM immunoglobulin covalently bound to a specific, non-IgM antibody, said specific, non-IgM antibody being directed against a specific infectious disease agent.

2. The positive calibrator or control composition as defined in claim 1 wherein said nonspecific IgM immunoglobulin is from a human nonspecific IgM immunoglobulin.

3. The positive calibrator or control composition as defined in claim 1 wherein said specific, non-IgM antibody is from a non-human IgG antibody.

4. The positive calibrator or control composition as defined in claim 1 wherein said composite antibody comprises a human nonspecific IgM immunoglobulin covalently linked to a specific IgG antibody.

5. The positive calibrator or control composition as defined in claim 1 wherein said specific, non-IgM antibody is from a monoclonal antibody.

6. The positive calibrator or control composition as defined in claim 1 wherein said specific, non-IgM antibody is IgG or the F(ab)$_2$ segment thereof.

7. The positive calibrator or control composition as defined in claim 1 wherein said specific, non-IgM antibody is from an antibody selected from the group consisting of HIV antibodies, HTLV antibodies, cytomegalovirus antibodies, toxoplasma antibodies, rubella antibodies, herpes antibodies, lyme disease antibodies and hepatitis antibodies.

8. The positive calibrator or control composition as defined in claim 1 wherein said composite antibody is made by reacting a nonspecific IgM immunoglobulin and a specific non-IgM antibody at a molar ratio of from about 1:1 to about 1:5.

9. The positive calibrator or control composition as defined in claim 8 wherein said composite antibody is made by reacting a nonspecific IgM immunoglobulin and a specific non-IgM antibody at a molar ratio of about 1:2.

10. The positive calibrator or control composition as defined in claim 1 and further including at least one additional composite antibody of a nonspecific IgM immunoglobulin covalently bound to a specific non-IgM antibody directed against a specific infectious disease agent, wherein each specific non-IgM antibody of each said composite antibody is directed against a different specific infectious disease agent.

11. A method for carrying out an assay with a positive calibrator or control composition for the presence of IgM antibodies to an infectious disease comprising the steps of:

(a) applying to a solid carrier (i) a positive calibrator or control composition which comprises composite antibodies, said composite antibodies comprising a nonspecific IgM immunoglobulin covalently bound to a specific, non-IgM, antibody directed against a specific infectious disease agent, and (ii) a labeled detector material said solid carrier having immobilized thereto a binding material which binds to said composite antibodies and wherein the detector material of said labeled detector material binds to said composite antibodies whereby there is formed a ternary complex of said immobilized binding material, said composite antibodies and said labeled detector material;

(b) removing free labeled detector material from said solid carrier; and (c) obtaining a readout signal by detecting the bound or free labeled detector material.

12. The method as defined in claim 11 wherein said binding material immobilized to said solid carrier binds to the nonspecific IgM immunoglobulin of said composite antibodies and said detector material of said labeled detector material binds to said specific, non-IgM antibody of said composite antibodies.

13. The method as defined in claim 11 wherein said binding material immobilized to said solid carrier binds to said specific, non-IgM antibody of said composite antibodies and said detector material of said labeled detector material binds to said nonspecific IgM immunoglobulin of said composite antibodies.

14. The method as defined in claim 11 wherein step (a) comprises applying said positive calibrator or control composition to said solid carrier, incubating said solid carrier and then applying said labeled detector material to said solid carrier.

15. The method as defined in claim 11 wherein step (a) comprises combining said positive calibrator or control composition with a solution of said labeled detector material, incubating the mixture and then applying said mixture to said solid carrier.

16. The method as defined in claim 11 wherein the label of said labeled detector material is a member of the group consisting of fluorescent materials, radioactive materials and enzymes.

17. The method as defined in claim 11 wherein said label is an enzyme and step (b) comprises applying to said solid carrier a solution of substrate material for said enzyme.

18. A method for determining a reference signal cutoff value for an assay for the presence of antibodies to an infectious disease agent comprising the steps of:

(a) applying to a solid carrier (i) a positive calibrator or control composition which comprises composite antibodies, said composite antibodies comprising a nonspecific IgM immunoglobulin covalently bound to a specific, non-IgM, antibody directed against a specific infectious disease agent, and (ii) a labeled detector material said solid carrier having immobilized thereto a binding material which binds to said composite antibodies and wherein the detector material of said labeled detector material binds to said composite antibodies whereby there is formed a ternary complex of said immobilized binding material, said composite antibodies and said labeled detector material;

(b) removing free labeled detector material from said solid carrier;

(c) obtaining a readout signal by detecting the bound or free labeled detector material; and (d) utilizing said readout signal in the determination of a reference signal cutoff value.

* * * * *